United States Patent [19]

Matsunaga et al.

[11] Patent Number: 4,465,664

[45] Date of Patent: Aug. 14, 1984

[54] HAIR SETTING COMPOSITION

[75] Inventors: Kinjiro Matsunaga, Miyashiro; Takeo Okumura, Sakura; Sachio Naito, Tokyo; Rikio Tsushima, Wakayama, all of Japan

[73] Assignee: Kao Corporation, Tokyo, Japan

[21] Appl. No.: 316,288

[22] Filed: Oct. 29, 1981

[30] Foreign Application Priority Data

Nov. 20, 1980 [JP] Japan .................... 55-163783

[51] Int. Cl.$^3$ .................. A61K 7/09; A61K 7/11; A61K 7/06; A61K 47/00
[52] U.S. Cl. ........................ 424/71; 424/70; 424/72; 424/359
[58] Field of Search ............... 424/70, 72, 71, 359

[56] References Cited

U.S. PATENT DOCUMENTS

| | | | |
|---|---|---|---|
| 3,961,634 | 6/1976 | Busch | 424/71 |
| 4,229,429 | 10/1980 | Johnson et al. | 424/70 |
| 4,272,511 | 6/1981 | Papantoniou et al. | 424/71 |
| 4,279,996 | 7/1981 | Yoshioka et al. | 424/70 |

FOREIGN PATENT DOCUMENTS 1392216 4/1964 France.
2438662 10/1979 France.

Primary Examiner—Jerome D. Goldberg
Assistant Examiner—Freda Abramson
Attorney, Agent, or Firm—Oblon, Fisher, Spivak, McClelland & Maier

[57] ABSTRACT

A hair setting composition is described which comprises at least one of decomposition products obtained by oxidation of keratin materials and derivatives at a thiol group of decomposition products obtained by reduction of keratin materials, and at least one of alkanolamines and basic amino acids. The member is dissolved in a polar solvent in an amount of 0.01 to 10 wt. % of the composition. The base is contained in a weight ratio to the member of 0.02 to 0.7:1.

7 Claims, No Drawings

HAIR SETTING COMPOSITION

BACKGROUND OF THE INVENTION

1. Field of the Invention

This invention relates to hair treatments, and more particularly, to a hair setting composition which shows an excellent set retention even under high humidity conditions.

2. Description of the Prior Art

Hair setting agents such as set lotions, hair sprays and the like are used to prevent the styled hair from getting out of shape owing to high humidity and wind. In known hair setting agents, there are used, as a fixing agent ensuring set retention, resinous components such as acrylic ester-methacrylic ester copolymers, polyvinylpyrrolidone-vinyl acetate copolymers and the like. However, it is known that these resinous components are hard to be washed away, so that they cannot be removed from hair completely even when the hair has been washed with shampoo. The components remaining on the surface of hair act to produce unfavorable phenomena such as an increase of a coefficient of friction of hair, occurrence of splits-ends or broken hairs by brushing, and lowering in texture of hair.

In order to overcome these drawbacks, there has been made an attempt in which nonionic surface active agents and/or wetting agents are added to the resinous components to increase the solubility in water. This method has, however, a vital drawback that though the detergency is improved, the set retention under high humidity is considerably lowered, impairing the inherent performance of the hair setting agent itself.

Accordingly, there is a demand of the development of a hair setting composition which can satisfy both requirements: (1) It shows an excellent set retention as to hold a hair style and (2) When hair is washed, the components are rapidly removed from hair.

On the other hand, keratin, which is a component such as of hair is made of epidermal cells, is a protein accumulated in the cells and is a compound in which cross-linkages are established between peptide chains by means of a multitude of disulfide bonds (—S—S). Attempts have been made to add the keratin or decomposition derivatives thereof to toiletries or cosmetics. However, the keratin itself is in the form of fibers, amorphus or a mixture thereof, and is insoluble in polar solvents such as water, alcohols and the like. Further, the decomposition derivatives obtained by reduction or oxidation of keratin are slightly soluble in polar solvents because of the presence of hydrogen bonds, ionic bonds and hydrophobic bonds between protein chains, so that only very dilute solutions are obtained, placing the limit on their applications.

SUMMARY OF THE INVENTION

It is according an object of the invention to provide a hair setting composition which shows excellent setting force and washability.

It is another object of the invention to provide a hair setting composition which makes use of modified keratin materials which are soluble in polar solvents and alkanolamines or basic amino acids.

It is a further object of the invention to provide a hair setting composition which ensures smooth brushing without impairing hair.

We have made extensive studies on keratin derivatives and found that coexistence of decomposition products obtained by oxidation of keratin materials or derivatives at the thiol group of decomposition products obtained by reduction of keratin materials (hereinafter referred to generically as "decomposition derivatives of keratin materials") and alkanolamines or basic amino acids (hereinafter referred to generically as "organic alkaline materials") results in a remarkable increase of the solubility in polar solvent and that a hair setting composition comprising these ingredients shows excellent setting force and washability.

According to the present invention, there is provided a hair setting composition comprising a member selected from decomposition products obtained by oxidation of keratin materials and derivatives at a thiol group of decomposition products obtained by reduction of keratin materials and a mixture thereof, and a base selected from the group consisting of alkanolamines, basic amino acids and a mixture thereof, the member having been dissolved in a polar solvent in an amount of 0.01 to 10 wt% of the composition, the base being contained in a ratio, to the member, by weight of 0.02 to 0.7:1.

DETAILED DESCRIPTION AND EMBODIMENTS OF THE INVENTION

The decomposition products obtained by oxidation of keratin material and derivatives at the thiol group of decomposition products obtained by reduction of keratin to be used in the present invention are prepared in the following manner and have an average molecular weight of 30,000–100,000.

The starting keratin materials include, for example, animal hair, human hair, feather, claw, horn, hoof and scale, among which wool, hair and feather are preferably used. These keratin materials may be subjected to the oxidation or reduction reaction as they are but, if necessary, may be cut or reduced into pieces of a suitable size or may be pretreated such as by washing and defatting.

(a) Decomposition product obtained by oxidation of keratin

The oxidation of keratin can be conducted by a variety of methods known per se (N. H. Leon; Textile Progress, Vol. 7, page 1 (1975)). Oxidizing agents are preferably organic or inorganic agents of the type which electrophilically acts on the disulfide bond (S—S bond) in the keratin structure. Examples of the oxidizing agents include organic peracids, inorganic peroxo acids or their salts, permanganic acid or its salts, chromic acid or related compounds, halogens, peroxides, oxyacids or their salts, and the like, among which the organic peracids such as peracetic acid, performic acid and perbenzoic acid are preferable.

The oxidation reaction is conducted in liquid media using oxidizing agents in excess with respect to the disulfide bonds in the keratin material, ordinarily in amounts over two equivalents or more, preferably 4–10 equivalents, of the disulfide bonds. The reaction is feasible under acidic or alkaline conditions and is preferably conducted under acidic conditions and particularly under weakly acidic conditions. The reaction temperature and pressure vary depending on the types of the oxidizing agent and keratin material and are not critical. Room temperature is generally sufficient but, if necessary, heat may be applied. An atmospheric pressure is sufficient but the reaction may be conducted under reduced pressure or under pressure.

By this, the disulfide bond of keratin material is cleft into sulfonic acid (—SO₃H).

(b) Derivatives at the thiol group of decomposition products obtained by reduction of keratin materials Reducing agents employed for reducing keratin materials are preferably organic or inorganic reducing agents of the type which serves to cleave the disulfide bond in the keratin structure into a thiol group (—SH) and generally acts nucleophilically on the disulfide bond. Examples of the reducing agents include organic reducing agents such as mercaptoethanol, thioglycollic acid, benzylmercaptan, 1,4-dithiothreitol, tributylphosphine and the like, and inorganic reducing agents such as sodium hydrogensulfite, sulfides such as sodium hydrosulfide, metallic hydrides such as lithium aluminium hydride.

The amount of the reducing agent is usually in the range of 2-10 equivalents of the disulfide bonds in keratin material. The pH of the reaction system is in the range of 2-12, preferably 6-11. Outside the range, the hydrolysis undesirably takes place at the same time. The reaction temperature is sufficient to be room temperature but heat may be applied to shorten the reaction time. The reaction time is ordinarily in the range of 2-3 hours or more. Since the thiol group produced by the reduction is required not to be substantially oxidized, the reduction operation should conveniently be carried out in an atmosphere of inert gas to give good results.

The decomposition product obtained by the reduction of keratin material is then chemically modified at the thiol group thereof to obtain a derivative thereof. The derivatives at the thiol group include:

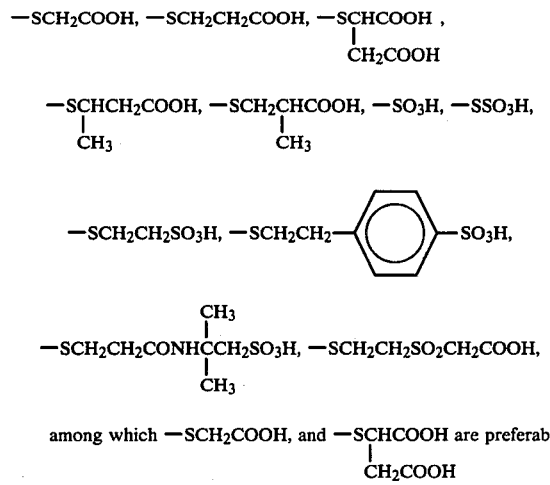

among which —SCH₂COOH, and —SCHCOOH are preferable.

The chemical modification of the thiol group is known per se and can be conducted, for example, based on the procedures known from N. H. Leon; Textile Progress, Vol. 7, page 1 (1975), "Yuki Ioo Kagobutsu (Organic Sulfur Compounds)" written by Shigeru Ookyo and published by Kagaku Dojin (1968) and "Kobunshi Jikkengaku Koza" written by Masami Oku, Vol. 12, Kyoritsu Shuppan (1957). Typical methods are shown below.

(1) Method utilizing the nucleophilic substitution reaction of SH group

K—SH+R—L, K—S—R+HL (in which K represents a residue of a keratin compound, R represents a chemically modifying group to be introduced, and L represents a leaving atom or group such as a halogen atom or acid residue).

Compounds which react by this method include, for example, halogen compounds such as iodoacetic acid, bromoacetic acid, chloroacetic acid and the like.

(2) Method utilizing the nucleophilic addition reaction of SH group with a double bond between carbon atoms

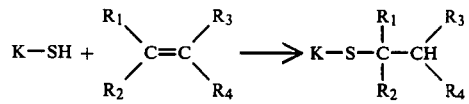

(in which at least one of $R_1$, $R_2$, $R_3$ and $R_4$ represents a carboxyl group or sulfonic acid group, the other represent an alkyl group or hydrogen atom, and K has the same meaning as defined hereinbefore).

Compounds which react by this method include, for example, acrylic acid, methacrylic acid, crotonic acid, maleic acid, fumaric acid, vinylcarboxylmethylsulfone, vinylsulfonic acid, styrenesulfonic acid, 2-acrylamido-2-methylpropanesulfonic acid and the like.

(3) Method using a substitution reaction between SH group and sulfite compound

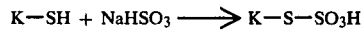

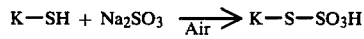

(in which K has the same meaning as defined hereinbefore).

(4) Method of oxidizing SH group into sulfonic acid group

(in which K has the same meaning as defined hereinbefore).

The oxidizing agents used in this reaction include, for example, halogens, permanganates and the like.

The organic alkaline materials to be used in the present invention include as the alkanolamine 2-amino-2-methyl-1-propanol (AMP), 2-amino-2-methyl-1,3-propanodiol (AMPD), 2-amino-2-ethyl-1,3-propanediol (AEPD), 2-amino-1-butanol (AB), triisopropanolamine (TIPA), diisopropanolamine (DIPA), monoisopropanolamine (MIPA), triethanolamine (TEA), diethanolamine (DEA), monoethanolamine (MEA) and the like, and as the basic amino acid: lysine, alginine, histidine, hydroxylysine and the like.

These organic alkaline materials may be added to the hair setting composition after having been converted into salts with the decomposition derivatives of keratin material, or may be separately added so as to allow the organic alkaline material and the derivative to coexist in the system.

Where it is desired to form salts between the decomposition derivatives of keratin material and the organic alkaline materials alkanolamines or basic amino acids are added to a filtrate which has been obtained by the oxidation reaction of keratin material or by the chemical modification reaction after the reduction of keratin material, followed by concentrating and freeze drying to obtain such salts.

The hair setting composition according to the present invention is prepared by admixing 0.01–10 wt% (hereinafter referred to simply as %), preferably 0.1–5%, of a decomposition product of keratin material and 0.1–8 equivalents of an organic alkaline material based on the carboxyl group or sulfonic acid group of the decomposition product of keratin material, i.e. the organic alkaline material being used in a weight ratio to the decomposition derivatives of keratin material of 0.02–0.7:1, and dissolving the mixture in a polar solvent such as water, ethyl alcohol, propyl alcohol or the like.

To the hair setting composition of the invention may be further added within limits as not to impede the effect of the invention arbitrary ingredients depending on intended purposes including, for example, oil materials such as higher alcohols, higher fatty acid esters and the like, nonionic surface active agents serving as emulsifier or solubilizer such as polyoxyethylene lauryl ether, monolauric acid polyoxyethylenesorbitan, polyoxyethylene hydrogenated castor oil and the like, moisturizing agents such as glycerine, propylene glycol and the like, perfumes, and colorants.

The hair setting composition according to the invention may directly be applied to hair as it is or may be sprayed by the use of a pump sprayer or may be filled in a container together with a spray such as a Freon gas, liquified petroleum gas, carbon dioxide or the like and applied in the form of a spray or foam.

The thus obtained hair setting composition according to the invention can make a uniform, tough film after drying and shows an excellent hair setting force or hair retention even under high humidity conditions and is readily removable from hair when the hair is washed with shampoos containing currently employed anionic active agents, thus satisfying both the setting force and wasability.

The present invention is particularly described by way of examples and references, which should not be construed as limiting the present invention thereto.

REFERENCE 1

Preparation of oxidation, decomposition derivatives of keratin materials (a) Ten grams of wool fibers were immersed in 700 g of 8% aqueous peracetic acid solution at room temperature for 1 day for the oxidation reaction. The resulting oxidized wool was filtered and washed with water, and then immersed in 700 g of a 0.1N ammoniacal solution at room temperature for 1 day, permitting about 90% of the wool to dissolve in the ammoniacal solution. About 1 g of the insoluble matters were removed by filtration and the aqueous ammoniacal solution of keratose as an oxidized decomposition product of wool keratin was admixed with 2N hydrochloric acid to have its pH of 4.0, whereupon $\alpha$-keratose was separated as a precipitate. This precipitate was filtered, washed with acetone and dried to obtain 5.4 g of $\alpha$-keratose.

(b) Wool fibers were heated under pressure in an autoclave by the use of saturated steam of 6 kg/cm$^2$ for 6 minutes and were abruptly released in the air to obtain a porous swollen matter. Ten grams of the swollen matter which had been reduced to pieces, 250 g of formic acid and 50 g of 30% aqueous hydrogen peroxide solution were charged into a 500 ml three neck distillation flask to immerse the pieces at room temperature for 1 day, whereupon no powder was found in the solution with the foam-like matter being floated on the upper layer. This reaction mixture was filtered and the filtrate was poured into 1.5 liters of water, followed by adding hydrochloric acid to adjust the pH to 4. The resulting precipitate was collected by filtration and washed with 500 ml of water to obtain 4.5 g of $\alpha$-keratose. To the insoluble matters from which the reaction product had been removed by filtration were added 350 ml of water and then an ammoniacal solution to adjust the pH to 11, and the matters were immersed at room temperature for 1 day. The system was filtered and the filtrate was added with hydrochloric acid to adjust the pH to 4. The resulting precipitate was collected by filtration to obtain 0.7 g of $\alpha$-keratose. It was found that 1.4 g of the insoluble matters were primarily made of $\beta$-keratose.

REFERENCE 2

Preparation of reduced, decomposition derivatives of keratin materials (a) Ten grams of wool fibers were immersed in 600 ml of an aqueous solution with concentrations of 8M urea and 0.01M Tris buffer, to which was added 6 ml of 2-mecraptoethanol, followed by adjusting the pH to 10 by means of a 5N potassium hydroxide aqueous solution to conduct the reduction reaction in an atmosphere of nitrogen at room temperature. About 3 hours after commencement of the reaction, the wool was allowed to dissolve in the reaction solution in an amount of about 85% thereof. While the system was adjusted with a 5N potassium hydroxide aqueous solution so as not to permit the pH below 7, 16.5 g of iodoacetic acid was gradually added and the pH of the system was finally adjusted to 8.5 to carry out the carboxymethylation reaction at room temperature for 2 hours. The reaction solution was filtered to remove insoluble matters therefrom and the resultant filtrate was charged into a cellulose tube wherein it was dialyzed against deionized water to remove low molecular weight impurities including urea. As the urea was dialyzed, the content in the cellulose tube was turned white since HGT (component with high contents of glycine and tyrosine) as a water-insoluble component was allowed to precipitate. After completion of the dialysis, the HGT was removed by centrifugal separation and S-carboxymethyl keratin (SCMKA) was obtained from the neutral transparent aqueous solution of SCMKA by the isoelectric precipitation method. That is, 1N hydrochloric acid was added to the system to adjust its pH to 4.4 by which SCMKA was turned insoluble and separated as precipitate. This precipitate was filtered, washed with ethanol and dried to obtain 4.2 g of SCMKA.

(b) The procedure of Reference 2-(a) was repeated except that there was used instead of wool fibers, feathers, which were heated for 6 minutes in an autoclave by means of superheated steam of 6 kg/cm$^2$ and 240° C. and then abruptly released in the air to obtain a porous swollen matter and that 1.75 g of maleic acid was used instead of iodoacetic acid, thereby obtaining 5.3 g of S-(1,2-dicarboxyethyl)-keratin.

(c) The procedure of Reference 2-(a) was repeated using a powder of hoof of horse instead of wool fibers and 11 g of acrylic acid instead of iodoacetic acid, thereby obtaining 4.2 g of S-(2-carboxyethyl)-keratin.

(d) The procedure of Reference 2-(a) was repeated using 28 g of styrenesulfonic acid instead of iodoacetic acid, thereby obtaining 4.8 g of S-(sulfophenylvinyl)keratin.

(e) Eight grams of wool fibers were dispersed in 300 ml of n-propanol and 300 ml of a 0.1N Tris buffer solution. After substitution with nitrogen, 3.2 ml of tri-n-butylphosphine was added, followed by agitating at room temperature for 24 hours. The solution was subjected to filtration. To the insoluble matter were added 400 ml of water, 9.28 g of maleic acid and about 30 ml of 5N potassium hydroxide to adjust the pH to 8.0, followed by agitating at room temperature for 6 hours. To the reaction system was added about 20 ml of a 28% aqueous ammoniacal solution to adjust the pH to 11.5, after which it was agitated at room temperature for 18 hours. The reaction solution was filtered to remove impurities therefrom and the resultant filtrate was placed in a cellulose tube in which it was dialyzed against deionized water to remove low molecular weight impurities therefrom. After completion of the dialysis, the insoluble matters in the cellulose tube were removed by centrifugal separation and the neutral transparent aqueous solution was adjusted to have a pH of 4.4 by addition of about 5.5 ml of 1N hydrochloric acid and the resulting precipitate was collected by filtration, followed by washing with ethanol and drying to obtain 3.9 g of S-(1,2-dicarboxyethyl)keratin.

(f) The procedure of Reference 2-(e) was repeated except that there was used instead of wool fibers a powder of a porous swollen matter which was obtained by heating wool in an autoclave by means of saturated steam of 6 kg/cm$^2$ for 6 minutes and that 16.5 g of 2-acrylamido-2-methylpropanesulfonic acid was used instead of maleic acid, thereby obtaining 4.5 g of keratin-S-(2-acrylamido-2-methylpropanesulfonic acid).

EXAMPLE 1

Hair setting compositions of the following formulations were prepared using the decomposition derivatives of the keratin materials obtained in References 1 and 2 to determine their set retention and washability.

| Formulation: | |
|---|---|
| Decomposition derivatives of keratin material (Table 1) | 1% |
| Organic alkali materials (Table 1) | 0.5 |
| Ethanol | 10 |
| Water-soluble silicone | 0.5 |
| Perfume | 0.1 |
| Water | balance |

Measuring Method (1) Set Retention

Tresses made of Japanese hair and having a length of 14 cm and a weight of 2 g were applied with the respective hair setting compositions shown in Table 1 in an amount of 1 g and were each wound on a glass rod with a diameter of 2.1 cm, followed by drying in a desiccator of phosphorus pentoxide for 24 hours. After complete drying, the rod was removed and each tress was suspended in an air-conditioned room of a temperature of 20° C. and a relative humidity of 95%. Thirty minutes after the suspension, the length of the formed curl was measured and the curl retention was calculated according to the following equation:

$$\text{Curl Retention (\%)} = \frac{Lo - Lt}{Lo - Ls} \times 100$$

in which, $Lo = 14$ (cm),
$Ls$ = Length of the curl immediately after the tress has been suspended at a humidity of 95% (cm),
$Lt$ = Length of the curl 30 minutes after the suspension under humidity conditions of 95%.

(2) Washability

The hairs used in test (1) were applied with 2 g of a shampoo composed of 15% of triethanolamine lauryl sulfate, 5% of lauryldiethanolamide and 80% of ion-exchanged water, lathered for 1 minute, rinsed with running water of 40° C. for 1 minute, and dried by means of a hand dryer. Then, 20 hairs were removed from each tress and observed under a scanning electron microscope as to whether or not the polymer or decomposition derivaive of keratin was left on the surface of hair. The results were expressed by a ratio of a number of hairs having the remaining matter thereon to the number of the observed hairs. Results are shown in Table 1 below.

TABLE 1

| Decomposition Derivative of Keratin Material | Organic Alkali Material | Set Retention (%) | Washability |
|---|---|---|---|
| Inventive Composition | | | |
| Decomposition derivative obtained by oxidation in reference 1-(a) (M.W. 60,000) | 2-amino-2-methyl-1-propanol (AMP) | 79 | 0/20 |
| Decomposition derivative obtained by oxidation in reference 1-(a) (M.W. 60,000) | 2-amino-2-methyl-1,3-propanediol (AMPD) | 85 | 0/20 |
| Decomposition derivative obtained by oxidation in reference 1-(a) (M.W. 60,000) | triisopropanolamine (TIPA) | 70 | 0/20 |
| Decomposition derivative obtained by oxidation in reference 1-(a) (M.W. 60,000) | triethanolamine (TEA) | 72 | 0/20 |
| Decomposition derivative obtained by oxidation in reference 1-(a) (M.W. 60,000) | lysine | 77 | 0/20 |
| Decomposition derivative obtained by oxidation in reference 1-(a) (M.W. 60,000) | alginine | 80 | 0/20 |
| Decomposition derivative obtained by oxidation in reference 1-(a) (M.W. 60,000) | histidine | 75 | 0/20 |
| Decomposition derivative obtained by oxidation in | hydroxylysine | 74 | 0/20 |

TABLE 1-continued

| Decomposition Derivative of Keratin Material | Organic Alkali Material | Set Retention (%) | Wash-ability |
|---|---|---|---|
| reference 1-(a) (M.W. 60,000) Control | | | |
| Decomposition derivative obtained by oxidation in reference 1-(a) (M.W. 60,000) Comparative composition | nil | 46 | 3/20 |
| Decomposition derivative obtained by oxidation in reference 1-(a) (M.W. 60,000) | sodium hydroxide | 56 | 1/20 |
| Decomposition product obtained by oxidation of collagen (M.W. 15,000) Inventive Composition | nil | 53 | 0/20 |
| Decomposition derivative obtained by reduction in reference 2-(a) (M.W. 40,000) | 2-amino-2-methyl-1-propanol (AMP) | 78 | 0/20 |
| Decomposition derivative obtained by reduction in reference 2-(a) (M.W. 40,000) | 2-amino-2-methyl-1,3-propanediol (AMPD) | 75 | 0/20 |
| Decomposition derivative obtained by reduction in reference 2-(a) (M.W. 40,000) | triisopropanolamine (TIPA) | 68 | 0/20 |
| Decomposition derivative obtained by reduction in reference 2-(a) (M.W. 40,000) | triethanolamine (TEA) | 70 | 0/20 |
| Decomposition derivative obtained by reduction in reference 2-(a) (M.W. 40,000) | lysine | 74 | 0/20 |
| Decomposition derivative obtained by reduction in reference 2-(a) (M.W. 40,000) | alginine | 78 | 0/20 |
| Decomposition derivative obtained by reduction in reference 2-(a) (M.W. 40,000) | histidine | 72 | 0/20 |
| Decomposition derivative obtained by reduction in reference 2-(a) (M.W. 40,000) Control | hydroxylysine | 72 | 0/20 |
| Decomposition derivative obtained by reduction in reference 2-(a) (M.W. 40,000) Comparative composition | nil | 43 | 4/20 |
| Decomposition derivative obtained by reduction in reference 2-(a) (M.W. 40,000) | sodium hydroxide | 52 | 0/20 |
| collagen commercially available set lotion | nil | 49 | 0/20 |

EXAMPLE 2

A blow styling lotion of the following formulation was prepared and evaluated by an evaluation panel consisting of 30 female members of 18–35 years old in which the set retention, feel of the finishing, and feel of residue after washing of hair were assessed by a paired comparison method using a comparative product.

| Formulation: | |
|---|---|
| Decomposition derivative of keratin material (obtained in Reference 1-(a)) | 2% |
| 2-amino-2-methyl-1-propanol | 1 |
| ethanol | 10 |
| water-soluble silicone | 0.5 |
| perfume | 0.1 |
| water | balance |
| (Comparative Composition) | |
| vinyl acetate-crotonic acid copolymer | 2% |
| triisopropanolamine | 1 |
| acid hydrolysate of collagen (M.W. 20,000) | 0.3 |
| ethanol | 10 |
| water | balance |

The results are shown in Table below.

TABLE 2

| | ITEM | | |
|---|---|---|---|
| EVALUATION | Set Retention | Feel of Finishing | Feel of Residue |
| Inventive composition being better | 10 | 11 | 22 |
| Inventive composition being slightly better | 17 | 18 | 6 |
| Hard to say whichever | 2 | 3 | 2 |
| Comparative composition being slightly better | 1 | 0 | 0 |
| Comparative composition being better | 0 | 0 | 0 |

(Note)
The values in the Table show the numbers of the panel member, respectively. The feel after washing was evaluated as good when the panel member had no feel of residue.

EXAMPLE 3

The blow styling lotion of the following formulations were prepared. The blow styling lotion were subjected to an evaluation of set retention, feel of finishing and feel after washing by the paired comparison method similarly to Example 2.

The decomposition derivatives of keratin materials and the results of the evaluation were shown in Tables 3 and 4, respectively.

| Formulation: | |
| --- | --- |
| Decomposition derivatives of keratin materials (Table 3) | 2% |
| 2-amino-2-methyl-1,3-propanediol | 1 |
| ethanol | 10 |
| water-soluble silicone | 0.2 |
| perfume | 0.1 |
| water | balance |

TABLE 3

Decomposition Derivatives of Keratin Materials

| Starting Material (Keratin Material) | Decomposing reagent (oxidizing and reducing agents) | Modifying Agent | Reference |
| --- | --- | --- | --- |
| 1 wool | peracetic acid | — | 1(a) |
| 2 swollen matter of wool | performic acid | — | 1(b) |
| 3 wool | 2-mercapto-ethanol | iodoacetic acid | 2(a) |
| 4 swollen matter of wool | 2-mercapto-ethanol | maleic acid | 2(b) |
| 5 pieces of horse's hoof | 2-mercapto-ethanol | acrylic acid | 2(c) |
| 6 wool | 2-mercapto-ethanol | styrene-sulfonic acid | 2(d) |
| 7 wool | tri-n-butyl-phosphine | maleic acid | 2(e) |
| 8 swollen matter of wool | tri-n-butyl-phosphine | 2-acrylamido-2-methyl-propanesulfonic acid | 2(f) |

Results:

TABLE 4

| Decomposition derivative of keratin material (sample No. of Table 3) | Set retention | Feel of finishing | Feel of residue |
| --- | --- | --- | --- |
| 1 | +1.7 | +1.8 | +1.8 |
| 2 | +1.6 | +1.8 | +1.9 |
| 3 | +1.8 | +1.8 | +1.8 |
| 4 | +1.7 | +1.7 | +1.8 |
| 5 | +1.5 | +1.6 | +1.7 |
| 6 | +1.6 | +1.7 | +1.9 |
| 7 | +1.6 | +1.7 | +1.7 |
| 8 | +1.7 | +1.8 | +1.9 |

(Note)
The values in the table show average values of the panel evaluated according to the following standard.
Evaluation standard:
+2 Inventive composition is better.
+1 Inventive composition is slightly better.
0 Hard to say whichever is better.
−1 Comparative composition is slightly better.
−2 Comparative composition is better.

EXAMPLE 4

Hair Liquid:

| (Formulation) | |
| --- | --- |
| Decomposition derivative of keratin material (obtained in reference 2(a)) | 5% |
| 2-amino-2-methyl-1,3-propanediol | 3 |
| ethanol | 40 |
| polypropylene oxide butyl ether | 5 |
| perfume | 0.3 |
| water | balance |

(Preparation)

The decomposition product of the keratin material was charged into a mixture of ethanol-water, to which was added 2-amino-2-methyl-1,3-propanediol while agitating to obtain an almost transparent solution. Thereafter, polypropylene oxide butyl ether and perfume were added to the solution, followed by sufficiently agitating to obtain a hair liquid.

This hair liquid showed an excellent set retention under high humidity conditions and good washability.

What is claimed is:

1. A hair setting composition comprising as the effective ingredient from 0.01 to 10 wt% of the decomposition product obtained by the oxidation of a keratin material selected from the group consisting of animal hair, human hair, wool fibers, feather, claw, horn and hoof and a basic material selected from the group consisting of 2-amino-2-methyl-1-propanol, 2-amino-2-methyl-1,3-propanediol, 2-amino-2-ethyl-1,3-propanediol, 2-amino-1-butanol, triisopropanolamine, diisopropanolamine, monoisoopropanolamine, triethanolamine, diethanolamine, monoethanolamine, lysine, arginine, histidine and hydroxylysine in an amount of from 0.02 to 0.7 to one part of the effective ingredient, the balance being a polar solvent selected from the group consisting of water, ethyl alcohol and propyl alcohol; said composition being soluble in said polar solvent.

2. The composition according to claim 1 wherein the oxidized decomposition product is present in amount of from 0.1 to 5 wt% of the composition.

3. The composition according to claim 1 wherein the oxidized decomposition product is in the form of a salt.

4. The composition according to claim 1 wherein the decomposition products have an average molecular weight of about 30,000–100,000.

5. The composition according to claim 1 wherein the keratin material is wool fibers.

6. The composition according to claim 1 wherein the keratin material is hoof.

7. The composition according to claim 1 wherein the keratin material is feather.

* * * * *